US012702387B2

(12) United States Patent
Fumagalli et al.

(10) Patent No.: US 12,702,387 B2
(45) Date of Patent: Aug. 11, 2026

(54) SWAB FOR COLLECTING SAMPLES OF BIOLOGICAL MATERIAL AND ASSOCIATE METHOD OF PRODUCTION

(71) Applicant: Copan Italia S.P.A., Brescia (IT)

(72) Inventors: Lorenzo Fumagalli, Brescia (IT); Giorgio Martello, Brescia (IT)

(73) Assignee: Copan Italia S.p.A., Brescia (IT)

( * ) Notice: Subject to any disclaimer, the term of this patent is extended or adjusted under 35 U.S.C. 154(b) by 397 days.

(21) Appl. No.: 18/290,254

(22) PCT Filed: May 9, 2022

(86) PCT No.: PCT/IB2022/054284
§ 371 (c)(1),
(2) Date: Nov. 10, 2023

(87) PCT Pub. No.: WO2022/238866
PCT Pub. Date: Nov. 17, 2022

(65) Prior Publication Data

US 2024/0225617 A1 Jul. 11, 2024

(30) Foreign Application Priority Data

May 12, 2021 (IT) ........................ 102021000012248

(51) Int. Cl.
*A61B 5/00* (2006.01)
*A61B 10/00* (2006.01)
*A61F 13/38* (2006.01)

(52) U.S. Cl.
CPC ...... *A61B 10/0051* (2013.01); *A61B 10/0096* (2013.01); *A61F 13/385* (2013.01)

(58) Field of Classification Search
CPC ............ A61B 10/0051; A61B 10/0096; A61B 2010/0216; A61F 13/385
See application file for complete search history.

(56) References Cited

U.S. PATENT DOCUMENTS 5,103,836 A * 4/1992 Goldstein .......... G01N 33/6854 206/569
5,910,122 A * 6/1999 D'Angelo .......... A61B 10/0051 600/580

(Continued)

FOREIGN PATENT DOCUMENTS

CN 110025335 A 7/2019
JP 2002-296153 A 10/2002

(Continued)

OTHER PUBLICATIONS

International Preliminary Report on Patentability in International Appln. No. PCT/IB2022/054284, mailed on Nov. 23, 2023, 8 pages.

(Continued)

*Primary Examiner* — May A Abouelela
(74) *Attorney, Agent, or Firm* — Fish & Richardson P.C.

(57) ABSTRACT

Swab (1) for collecting samples of biological material, comprising: —an elongated body (2), having at least a portion with substantially axial development, —a collection element (3) for samples of biological material, positioned on the elongated body (2), wherein the collection element (3) is configured for, and destined to, being introduced within the mouth of a subject and is configured for collecting and retaining and/or preserving a sample of biological material, in particular saliva of the subject, —an engagement element (5), in particular a stopper, positioned in correspondence of a predefined portion of the elongated body (2), the engagement element (5) being configured for being held, in use, by a subject and for being removably engaged with a container (7) for samples of biological material, wherein the engagement element (5) comprises a fragrance (102) and is configured for causing, in use, a stimulation of the production of saliva when brought near the nose of the subject.

16 Claims, 4 Drawing Sheets

(56) References Cited

U.S. PATENT DOCUMENTS

| | | | | |
|---|---|---|---|---|
| 6,133,036 | A * | 10/2000 | Putcha | B01L 3/5082<br>435/2 |
| 7,387,899 | B1 * | 6/2008 | D'Angelo | A61B 10/0051<br>435/287.7 |
| 2001/0008614 | A1 * | 7/2001 | Aronowitz | A61J 1/05<br>436/178 |
| 2002/0127143 | A1 * | 9/2002 | Kuo | A61B 10/0051<br>600/584 |
| 2003/0175993 | A1 * | 9/2003 | Toranto | A61B 10/0051<br>435/7.1 |
| 2004/0220498 | A1 * | 11/2004 | Li | A61B 5/6896<br>600/349 |
| 2004/0237674 | A1 | 12/2004 | Wu et al. | |
| 2008/0020477 | A1 * | 1/2008 | Pronovost | A61B 5/14532<br>436/95 |
| 2008/0305548 | A1 | 12/2008 | Gould et al. | |
| 2011/0204084 | A1 * | 8/2011 | Aronowitz | B01L 3/5029<br>422/547 |
| 2013/0209993 | A1 * | 8/2013 | Aronowitz | B01L 3/5021<br>435/5 |
| 2015/0216471 | A1 * | 8/2015 | Goldstein | A61B 5/682<br>600/573 |
| 2018/0299358 | A1 * | 10/2018 | Bazemore | G01N 1/405 |
| 2019/0008489 | A1 | 1/2019 | Trivia | |
| 2020/0022684 | A1 * | 1/2020 | Sessions | B01L 3/50825 |
| 2020/0196994 | A1 * | 6/2020 | Fougere | A61B 10/0051 |
| 2023/0349009 | A1 * | 11/2023 | Wallerstorfer | C12Q 1/6806 |

FOREIGN PATENT DOCUMENTS

| | | |
|---|---|---|
| WO | WO 2004/086979 A1 | 10/2004 |
| WO | WO 2008/131033 | 10/2008 |
| WO | WO 2015/159089 | 10/2015 |

OTHER PUBLICATIONS

International Search Report and Written Opinion in International Appln. No. PCT/IB2022/054284, mailed on Sep. 7, 2022, 11 pages.

Office Action in Italian Application No. 102021000012248, mailed on Feb. 11, 2022, 20 pages (with English Translation).

Office Action in Canada Appln. No. 3219062, mailed on May 5, 2025, 7 pages.

Office Action in Japanese Appln. No. 2023-568731, mailed on Apr. 21, 2026, 7 pages (with English translation).

* cited by examiner

SWAB FOR COLLECTING SAMPLES OF BIOLOGICAL MATERIAL AND ASSOCIATE METHOD OF PRODUCTION

CROSS-REFERENCE TO RELATED APPLICATION(S)

This application is a U.S. National Phase Application under 35 U.S.C. § 371 and claims the benefit of priority to International Application Serial No. PCT/IB2022/054284, filed May 9, 2022, which claims priority to Italian Application Serial No. 102021000012248, filed May 12, 2021, the contents of which are hereby incorporated by reference.

FIELD OF THE ART

The present disclosure refers to the field of devices for biological use and in detail concerns a swab for collecting samples of biological material, in particular for collecting saliva.

The present disclosure also relates to a method of production of a swab for collecting samples of biological material.

BACKGROUND ART

Swabs for collecting samples of biological material are traditionally used for collecting these samples directly from a subject. Known swabs of samples of biological material permit to identify the presence of viruses, for example HIV or coronavirus.

Nowadays, swabs for collecting samples of biological material are used either in the medical field, for example for routine examinations or in emergency procedures, or by law enforcement agencies for surveying for example places of criminal activity.

In particular, swabs for collecting samples of biological material are known, which are configured for permitting the collection of saliva from a subject. These devices typically comprise a sample collection element which is configured for collecting and retaining a predefined amount of saliva.

Swabs for collecting saliva from the user are used for example to carry out tests for substances of abuse, in particular anti-drug tests.

With specific reference to the collection of saliva, it has been noted that a known problem with swabs for collecting samples of biological material is associated with the phenomenon of dry mouth or poor salivation, wherein an insufficient amount of saliva is temporarily present in the mouth of the user. The phenomenon of dry mouth or poor salivation can be due to a plurality of factors, including emotional factors and/or due to the intake of certain medications or drugs.

Swabs for collecting samples of biological material are known wherein the collection element is impregnated with a substance configured for increasing saliva production. These devices are characterized by certain drawbacks.

In particular, in order to preserve the saliva sample collected by means of the collection element, it is preferable that this collection element is maintained free of foreign substances or even maintained sterile. The use of substances configured for increasing saliva production in the collection element can in fact raise biocompatibility issues or can alter the saliva sample, misleading subsequent chemical and/or biological analyses that are performed on the sample.

Therefore, the purpose of the present disclosure is to describe a swab for collecting samples of biological material, which solves the drawbacks described above.

Furthermore, the purpose of the present disclosure is to describe a method of production of a swab for collecting samples of biological material, which permits to solve the above described drawbacks.

SUMMARY

The object of the disclosure is now described in some of its salient aspects, which can be combined with each other or with portions of the description and/or claims.

Swab

According to the present disclosure it is first of all described a swab (1) for collecting samples of biological material, comprising:

- an elongated body (2), having at least a portion with substantially axial development,
- a collection element (3) for samples of biological material, positioned on the elongated body (2), preferably near one ending of the elongated body (2), wherein the collection element (3) is configured for, and destined to, being introduced within the mouth of a subject and is configured for collecting and retaining and/or preserving a sample of biological material, in particular saliva of the subject,
- positioned in correspondence of a predefined portion of the elongated body (2), the engagement element (5) being configured for being held, in use, by a subject and for being removably engaged with a container (7) for samples of biological material for closing said container (7),
- wherein the engagement element (5) comprises a fragrance (102) and is configured for causing, in use, a stimulation of the production of saliva when brought near the nose of the subject.

According to a further non-limiting aspect, the engagement element is configured for, and destined to, remain outside the mouth of the subject, and in particular near the nose of the subject, during the collection of the sample of biological material, in particular during the collection of saliva, from the subject.

According to a further non-limiting aspect, the fragrance (102) is distributed in at least part of the volume, preferably in all of the volume, of the engagement element (5).

According to a further non-limiting aspect, the fragrance (102) is uniformly distributed in said at least part of the volume, preferably in all of the volume, of the engagement element (5).

According to a further non-limiting aspect, the engagement element (5) is realized by mixing and subsequent melting at least pellets and/or granule (100) of polymeric material and at least said fragrance (102).

According to a further non-limiting aspect, said fragrance (102) is exclusively comprised in said engagement element (5) and is absent in the remaining parts of the swab.

According to a further non-limiting aspect, the engagement element (5) comprises a percentage substantially comprised between 0.1% and 10% in weight or in volume of fragrance (102) or between 0.5% and 7% in weight or in volume of fragrance (102), in particular a percentage substantially comprised between 1% and 6% in weight or in volume of fragrance (102), more preferably a percentage substantially comprised between 2% and 5% in weight or in volume of fragrance (102).

According to a further non-limiting aspect, at least the engagement element (5) comprises a dye (103), distributed in at least part of, preferably in all of, the volume of the engagement element (5), in particular wherein the dye (103) is uniformly distributed in said at least part of, preferably in all of, the volume of the engagement element (5).

According to a further non-limiting aspect, the engagement element (5) comprises a percentage substantially comprised between 0.2% and 5% in weight or in volume of dye (103), in particular a percentage substantially comprised between 0.5% and 4% in weight or in volume of dye (103), more in particular a percentage substantially comprised between 1% and 3% in weight or in volume of dye (103).

According to a further non-limiting aspect, the collection element (3) comprises an absorbing material, in particular an absorbing sponge or an absorbing fiber element or a flocked fiber absorbing element, configured for retaining in use a determined amount of fluid.

According to a further non-limiting aspect, the collection element (3) is realized in at least one among the materials of the following list: sponge, polyurethane sponge, urethane polyester sponge, rayon, polyester, carbon fiber, alginate, cotton, silk.

According to a further non-limiting aspect, the absorbing material configured and sized for retaining in use an amount of biological material, in particular saliva, comprised between 50 μl and 10 ml, preferably between 100 μl and 5 ml, more preferably between 200 μl and 2 ml and even more preferably between 500 μl and 1 ml.

According to a further non-limiting aspect, the collection element (3) is a sponge element.

According to a further non-limiting aspect, the collection element (3) is free from preserving substances and/or additives.

According to a further non-limiting aspect, the swab (1) is configured and destined to collect samples from human beings.

According to a further non-limiting aspect, the swab (1) is configured and destined to collect samples from animals and/or is configured for, and destined to, a veterinary use.

According to a further non-limiting aspect, the engagement element (5) is configured for being removably engaged with a container (7) for samples of biological material by contrast insertion and/or by screwing on said container (7) for samples of biological material, for closing the container (7).

According to a further non-limiting aspect, the engagement element (5) is realized by molding, in particular injection molding or compression molding or injection compression molding or by co-molding, of pellets and/or granule (100) of polymeric material and of at least said fragrance (102).

According to a further non-limiting aspect, the engagement element (5) is realized by molding at a temperature substantially comprised between 150° C. and 300° C., more preferably substantially comprised between 160° C. and 280° C., even more preferably substantially comprised between 220° C. and 275° C. or between 240° C. and 260° C.

According to a further non-limiting aspect, the fragrance (102) is originated from pellets and/or granule and/or a fluid of fragrance (102), in particular from pellets and/or granule and/or a fluid containing essential oil of the fragrance (102).

According to a further non-limiting aspect, the fragrance (102) is a fragrance of a food product and/or comprises one or more of the flavors from the following list: orange, dark or milk chocolate, strawberry, blueberries, meat, in particular chicken.

According to a further non-limiting aspect, the engagement element (5) and/or the pellet and/or granule of polymeric material comprises or is composed by at least one of the materials of the following list: polypropylene, polyethylene, PVC, polyester, nylon, polyamide, polystyrene.

According to a further non-limiting aspect, said polyethylene is a high-density polyethylene and/or is a polyethylene with antioxidant properties and/or with high thermal stability during the step of transformation.

According to a further non-limiting aspect, the polyethylene is a polyethylene with melting temperature substantially comprised in the range 130° C.-140° C.

According to a further non-limiting aspect, the polyethylene has an embrittlement temperature, optionally measured according to ASTM D 746 standard, lower than −30° C., preferably lower than −40° C., more preferably lower than −50° C.

According to a further non-limiting aspect, the engagement element (5) comprises a threaded portion; said threaded portion is configured for coupling with a counter thread present in correspondence on the container (7), optionally in correspondence of a collar (11) of the container (7).

According to a further non-limiting aspect, the dye (103) comprises inorganic pigments.

According to a further non-limiting aspect, the dye (103) is originated from pellets of polymeric material, in particular from polyethylene pellets, more specifically from high-density polyethylene pellets.

According to a further non-limiting aspect, the engagement element (5) comprises a hole within which is at least partially introduced the elongated body (2).

According to a further non-limiting aspect, the hole is configured for permitting the introduction of the elongated body (2) by contrast insertion.

According to a further non-limiting aspect, the engagement element (5) comprises an engagement surface, in particular a lateral engagement surface, destined in use to exert a sliding friction with a portion of the container (7).

According to a further non-limiting aspect, the engagement element (5) and the elongated body (2) are integral or are fixed and made integral.

According to a further non-limiting aspect, the dye (103) comprises inorganic pigments, or comprises organic pigments, or comprises organic and inorganic pigments.

Kit

According to the present disclosure it is described a kit comprising a swab (1) according to one or more of the present aspects, and a container (7) for samples of biological material, said container (7) comprising a cavity configured for containing at least a portion of said swab (1), in particular at least the collection element (3) of the swab (1).

According to a further non-limiting aspect, the container (7) comprises a body realized in a material configured for not permitting the diffusion of said fragrance (102) and/or configured for not absorbing said fragrance (102).

According to a further non-limiting aspect, the material of the container is a plastic material and/or is a transparent or translucent material.

Method

According to the present disclosure it is therein described a method of production of a swab (1) for collecting samples of biological material, comprising:

- a step of production of an elongated body (2) of the swab (1), the elongated body (2) having at least a portion with substantially axial development and being configured for supporting at least a collection element (3) of samples of biological material, in particular saliva of a subject,
- a step of production of a collection element (3), comprising realizing the collection element (3) on the elongated body (2) and/or followed by an assembly of the collection element (3) on the elongated body (2),
- a step of production of an engagement element (5), in particular a stopper, configured for being held, in use, by a subject and configured for, and destined to, being removably engaged with a container (7) for samples of biological material, comprising realizing the engagement element (5) on the elongated body (2) and/or followed by an assembly of the engagement element (5) to the elongated body (2),
- the step of production of the engagement element (5) comprising an addition of a fragrance (102), such that, in use, the approaching of the engagement element (5) to the nose of the subject determines a stimulation of the production of the saliva.

According to a further non-limiting aspect, the step of production of the engagement element (5) comprises a distribution of the fragrance (102) in at least part of, preferably in all of, the volume of the engagement element (5), in particular comprising a uniform distribution in said at least part of, preferably in all of, the volume of the engagement element (5).

According to a further non-limiting aspect, the step of production of the engagement element (5) comprises a mixing and a subsequent melting of at least pellets and/or granule (100) of polymeric material and of at least said fragrance (102).

According to a further non-limiting aspect, the addition of the fragrance (102) takes place exclusively in said engagement element (5) and is absent in the remaining parts of the swab.

According to a further non-limiting aspect, the step of production of the engagement element (5) comprises the addition of a percentage substantially comprised between 0.1% and 10% in weight or in volume of fragrance (102) or between 0.5% and 7% in weight or in volume of fragrance (102), in particular a percentage substantially comprised between 1% and 6% in weight or in volume of fragrance (102), more preferably a percentage substantially comprised between 2% and 5% in weight or in volume of fragrance (102).

According to a further non-limiting aspect, the step of production of the engagement element (5) comprises the addition of a dye (103), and comprises the distribution of the dye (103) in at least part of, preferably in all of, the volume of the engagement element (5), in particular comprising a uniform distribution of the dye (103) in said at least part of, preferably all of, the volume of the engagement element (5).

According to a further non-limiting aspect, at least the step of production of the engagement element (5) comprises a molding or an injection molding or a compression molding or an injection compression molding or a co-molding, of said pellets and/or granule (100) of polymeric material and of at least said fragrance (102).

According to a further non-limiting aspect, the addition of the fragrance (102) comprises the addition of pellets and/or granule and/or a fluid of fragrance (102), in particular of pellets and/or granule and/or a fluid containing essential oil of the fragrance (102).

According to a further non-limiting aspect, the molding, in particular the injection molding or compression molding or injection compression molding, or co-molding comprises a melting of said pellets and/or granule and of said fragrance (102) that takes place at a temperature substantially comprised between 150° C. and 300° C., more preferably substantially comprised between 160° C. and 280° C., even more preferably substantially comprised between 220° C. and 275° C. or between 240° C. and 260° C.

According to a further non-limiting aspect, the addition of the dye (103) comprises the addition of a percentage substantially comprised between the 0.2% and the 5% in weight or in volume of the dye (103), in particular a percentage substantially comprised between 0.5% and 4% in weight or in volume of the dye (103), more in particular a percentage substantially comprised between 1% and 3% in weight or in volume of the dye (103).

According to a further non-limiting aspect, the step of production of the collection element (3) comprises realizing an absorbing material, in particular an absorbing sponge or an absorbing fiber element or a flocked fiber absorbing element, configured for retaining in use a determined amount of fluid.

According to a further non-limiting aspect, the step of production of the collection element (3) comprises realizing said collection element (3) in the shape of a spongy element.

According to a further non-limiting aspect, the step of production of the collection element (3) comprises realizing the collection element (3) free of preserving substances and/or additives.

According to a further non-limiting aspect, the method comprises a step of realizing a threaded portion on said engagement element (5), said threaded portion being configured for coupling with a counter thread present in correspondence on the container (7), optionally in correspondence of a collar (11) of the container (7).

According to a further non-limiting aspect, the addition of said dye (103) comprises an addition of a dye (103) comprising organic pigments, or inorganic pigments, or organic and inorganic pigments.

According to a further non-limiting aspect, the addition of a dye comprises the addition of dye pellets (103) in polymeric material, in particular, polyethylene pellets, more specifically high-density polyethylene pellets.

According to a further non-limiting aspect, the step of production of the engagement element (5) comprises realizing a hole in the engagement element (5), and the method comprises a step of introduction of the elongated body (2) within said hole.

According to a further non-limiting aspect, the step of introduction of the elongated body (2) within the hole is a step of contrast insertion.

According to a further non-limiting aspect, the step of production of the engagement element (5) comprises realizing on the engagement element (5) an engagement surface, in particular a lateral engagement surface, destined in use to exert a sliding friction with a portion of the container (7).

According to a further non-limiting aspect, the method comprises a step of realizing the engagement element (5) and of the elongated body (2) in such a way that they are integral.

FIGURES

The object of the present disclosure is described therein in some of its preferred and non-limiting embodiments, with reference to the attached figures. A brief description of the figures is provided hereinafter.

DETAILED DESCRIPTION

Figures 1, 2:
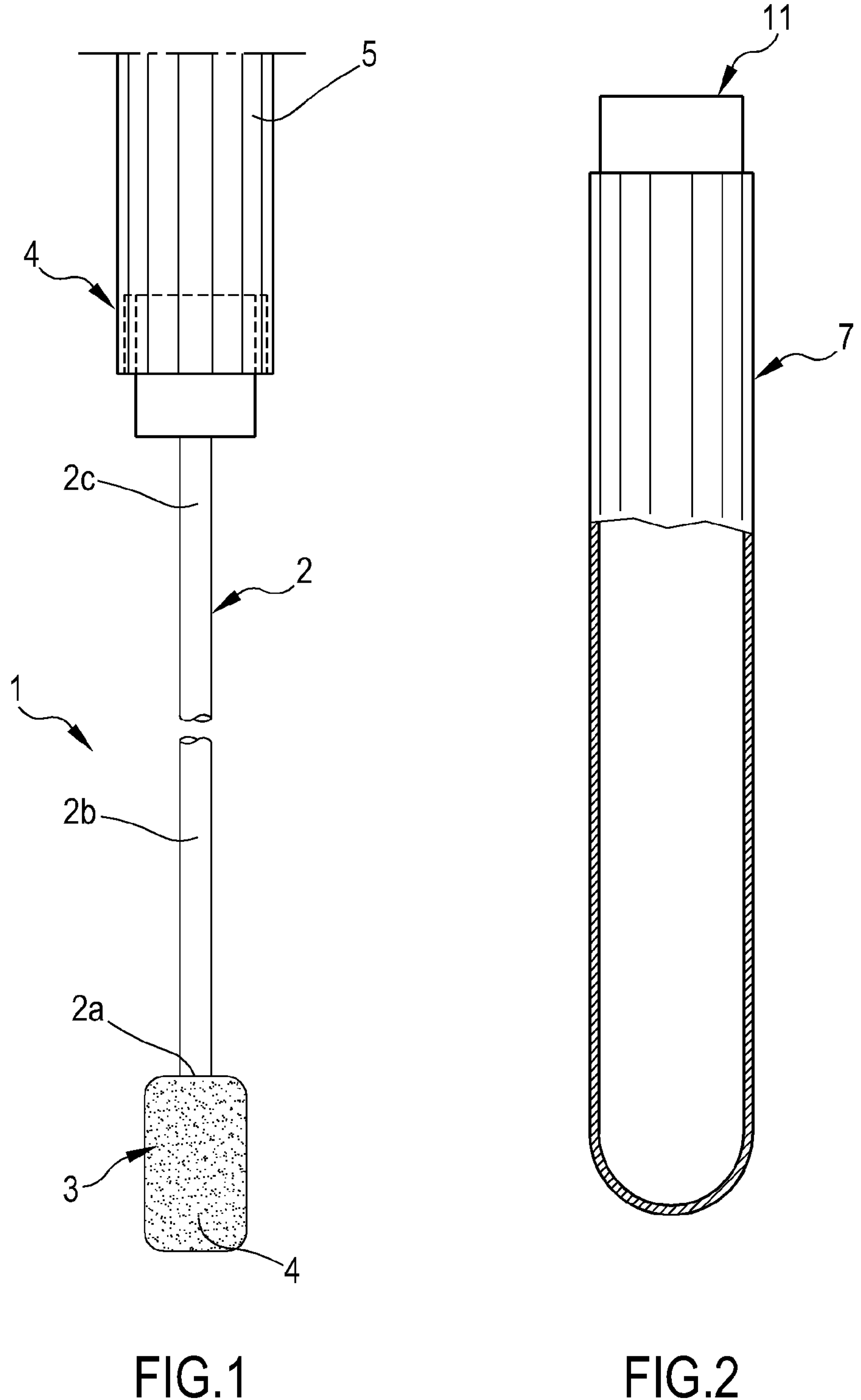
FIG. 1 shows a lateral view of a first embodiment of a swab for collecting samples of biological material according to the present disclosure.
FIG. 2 shows a partial sectional view of a container destined to contain at least part of the swab for collecting samples of biological material according to the present disclosure.

With reference to FIGS. 1 and 2, with reference number 1 is indicated as a whole a swab 1 for collecting samples of biological material.

The swab 1 comprises an elongated body 2 which defines a preferably but not limited thereto cylindrical transversal section rod.

In the attached figures the elongated body 2 has a substantially axial extension. This should not be intended in a limiting manner, as in general at least a portion of said elongated body 2 can have an axial extension, while remaining portions of it can have a curvilinear or other form profile.

The elongated body comprises a first portion 2*c*, defining a first ending of the elongated body 2 and a second portion 2*b* defining a second ending of the elongated body 2. The elongated body can show a longitudinal extension substantially comprised between 2 cm and 20 cm, or between 3 cm and 18 cm, or between 6 cm and 16 cm. The transversal section of the elongated body can be substantially inscribed in a circumference with a diameter comprised between 0.5 mm and 5 mm, or comprised between 1 mm and 3 mm, or comprised between 1.5 mm and 2.5 mm.

With reference to the annexed figures, the first end portion is the upper portion and the second end portion is the lower portion. The second ending of the elongated body is identified by the reference 2*a*.

The swab 1 further comprises a collection element 3 of samples of biological material. This collection element 3 is configured for, and destined to, collecting and retaining and/or preserving a sample of biological material, in particular saliva of a subject; therefore, the collection element 3 is configured for being in use introduced within the mouth of a subject. For this reason the collection element 3 is realized in a material compatible with the application, in particular biocompatible. Further construction details of the collection element 3 are described hereinafter.

The collection element 3 is positioned on the elongated body 2, and in particular is positioned in correspondence of the second portion 2*b* of the elongated body. In the embodiment shown in FIG. 1, the collection element 3 is positioned in substantial correspondence of the second ending 2*a* of the elongated body 2.

In particular, the collection element 3 can be glued by means of an adhesive on the second ending 2*a* of the elongated body. As shown in detail in FIG. 2, the collection element 3 can therefore surround the second ending 2*a* of the elongated body 2.

The collection element 3 comprises an absorbing material, in particular an absorbing sponge or an absorbing fiber or a flocked fiber absorbing element; this absorbing material is configured for retaining in use a determined amount of fluid for example an amount of biological material, in particular saliva, comprised between 50 μl and 10 ml, preferably between 100 μl and 5 ml, more preferably between 200 μl and 2 ml and even more preferably between 500 μl and 1 ml.

Preferably, this absorbing material can comprise at least one among the materials of the following list: sponge, polyurethane sponge, urethane polyester sponge (in particular, DegraPol®), rayon, polyester, carbon fiber, alginate, cotton, silk.

In a particular and non-limiting embodiment, the collection element 3 is realized through a flocked fiber absorbing element.

In a peculiar, non-limiting, embodiment, the collection element 3 is free from preserving substances and/or additives. This advantageously permits to maintain a high level of purity of the saliva sample collected.

The collection element 3 is specifically destined to retain a determined amount of saliva in order to carry out on the latter molecular tests and/or antigenic tests and/or antibody detection tests and/or hormonal evaluation tests and/or tests for substances of abuse. For example, but not limited thereto, these substances of abuse comprise for example and not limited thereto amphetamines, benzodiazepines, cocaine, methamphetamines, MDMA, opiates, in particular morphine, cannabinoids.

Figures 3, 4, 5:
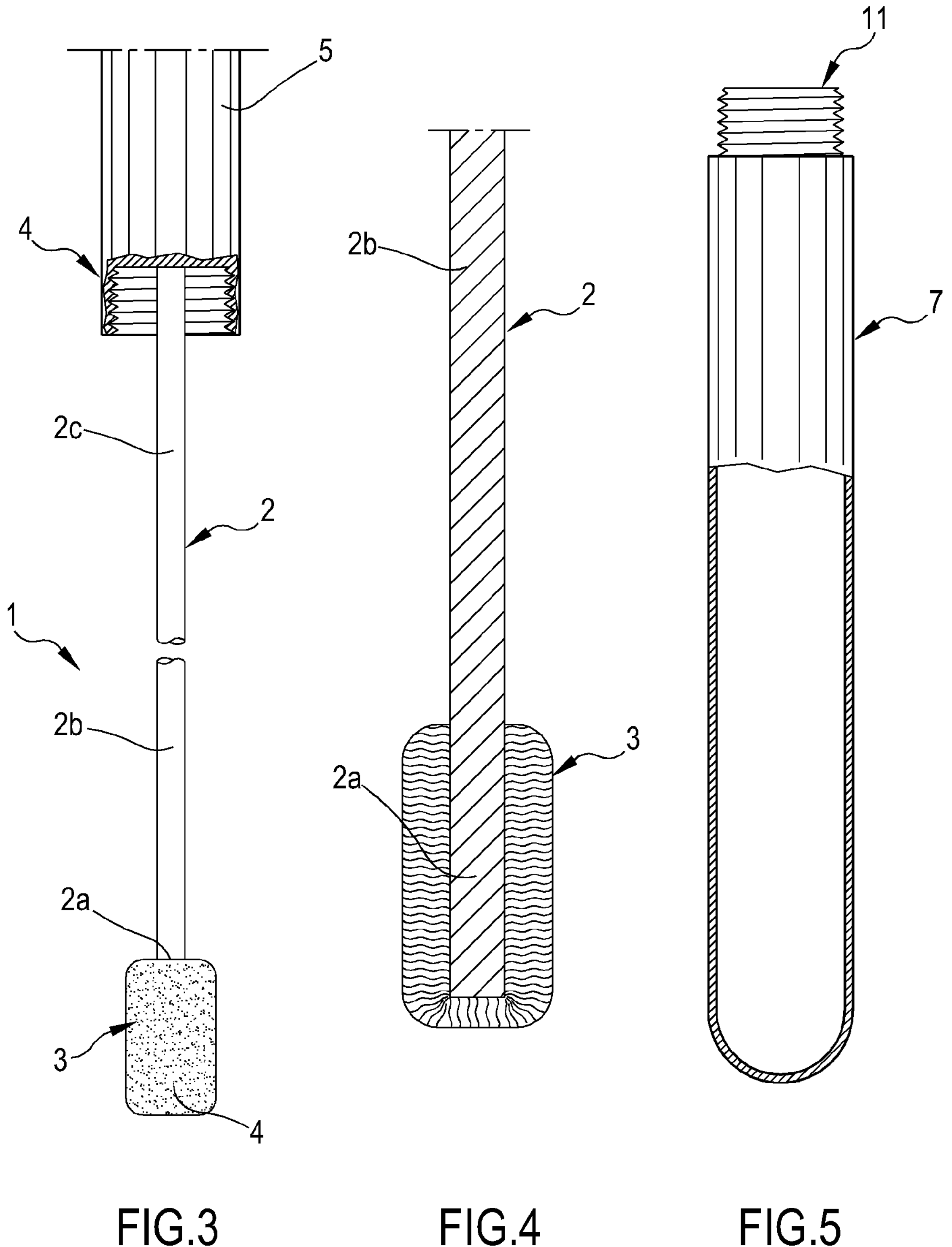
FIG. 3 shows a lateral view of an alternative embodiment of the swab for collecting samples of biological material according to the present disclosure.
FIG. 4 shows a sectional detail view of a collection element of the swab for the collection of FIG. 3.
FIG. 5 shows a partial sectional view of another embodiment of the container destined to contain at least part of the swab for collecting samples of biological material according to the present disclosure.

In the embodiment shown in FIGS. 1, 3 and 4 the second ending 2*a* of the elongated body has a substantially uniform transversal section, in particular a diameter. Consequently, the collection element 3 also detects a substantially uniform transversal section.

The swab 1 further comprises an engagement element, in particular a stopper 5. During the present detailed description, specific reference will be made to stopper 5, but any feature relating to stopper 5 shall generally be intended to be present for any engagement element. The engagement element is configured for being held, in use, by a subject and for being removably engaged with a container 7 for samples of biological material.

In detail the stopper 5 is positioned in correspondence of a predefined portion of the elongated body 2. In the embodiments shown in FIGS. 1, 3 and 4, the stopper 5 is positioned in substantial correspondence of the first portion 2*c* of the elongated body 2, and lies in substantial correspondence of the first ending of the elongated body 2.

The stopper 5 is configured for being removably engaged with a container 7 for samples of biological material. The stopper 5 is also configured for acting as engagement element configured for permitting to the user to hold the swab 1 on a surface of sufficient transversal section to ensure a firm engagement with the user's fingers.

In the embodiment shown in FIG. 1, the stopper 5 comprises a hole within which is at least partially introduced the elongated body 2; the transversal section of this hole is sufficient to determine a contrast insertion of the elongated body 2, in particular of the first portion 2*c* of the elongated body 2 sufficient to cause an effective retention of this portion in the stopper 5. This particular constructive configuration must not be intended in a limiting manner, as the Applicant has conceived further embodiments of the swab 1 wherein the stopper 5 and the elongated body 2 are made integral by means of a non-removable coupling or are integral, i.e. are indivisibly connected, for example and not limited thereto as they are realized through a single process of production and/or are seamlessly joined.

The stopper 5 comprises an engagement portion configured for removably engaging with a collar 11 of the container 7. In the embodiment shown in FIGS. 1 and 2, the engagement portion has a substantially cylindrical transversal section and is configured and specifically destined to couple with the collar 11 by means of an axial introduction within the container 7, realizing, in use, a substantially grazing friction force with an inner surface of the collar. Optionally, the engagement portion can have a knurling, destined to cause an increase in the friction force required for the coupling or removal of the collar 11.

An alternative embodiment of the swab 1 is shown in FIGS. 3, 4 and 5. In detail, in this case the stopper 5 comprises a threaded portion; this threaded portion is configured for coupling with a counter thread present in correspondence of the collar 11 of the container 7.

In the specific embodiment shown in FIG. 3 the thread present on stopper 5 is male while the thread present on collar 11 is a female counter-thread, in this case arranged in substantial correspondence of the inner surface of collar 11. Alternatively, the thread present on stopper 5 is female, and the counter-thread present on collar 11 is a male counter-thread.

The stopper 5 comprises an outer surface that can optionally be provided with a non-slip knurling and/or destined to increase the friction with the user's fingers.

Independently of shape and mechanical structure, the stopper 5 of the swab comprises a fragrance 102 and is configured for causing, in use, a stimulation of the production of the saliva.

The Applicant observes that in use the stopper 5 always lies outside the mouth of the user, in particular because it is held by the user or an operator. Therefore the stopper 5 is not in contact with saliva, in particular with the portion of saliva which, retained in the collection element 3, is destined to subsequent analysis. This allows to maintain the saliva pure, avoiding direct contact with said fragrance which might, otherwise, alter its chemical or biological composition. Furthermore, this allows to avoid problems of biocompatibility certification of the fragrance, which would otherwise be necessary to obtain for practical purposes should the fragrance be comprised in other portions of the swab 1. However, the stopper 5 is positioned sufficiently close to the mouth and nose to permit to the user to feel the fragrance and thus to have the desired stimulation effect of production of the saliva. In particular, the fragrance is only present in the stopper 5.

Although in general any fragrance destined to allow a stimulation of saliva production can be used, preferably this fragrance is the fragrance of a food product or is one of the fragrances of the following list: orange, dark or milk chocolate, strawberry, blueberries, meat, in particular chicken.

The fragrance is distributed in at least part of the volume of the stopper 5. Preferably, the fragrance is uniformly distributed in all of the volume of stopper 5. This allows to load a significant amount of fragrance, and to have a stimulating effect on production of the saliva that can be maintained for a long time, even when the stopper 5 is not isolated from the external environment. The Applicant observes that under certain preservation conditions, the fragrance charge present in the volume of the stopper 5 is sufficient to cause, in use, a sufficient stimulus to saliva production even after a storage time at least equal to 3 months, or 4 months, or 6 months, or 12 months, or 16 months or 18 months or more. In particular this storage time can be a storage time of swab 1 within an appropriate container, for example and not limited thereto a flexible container. Preferably, but not limited thereto, this container is a container in plastic material, optionally in sheet, configured for being insulated from the external environment in such a way as to provide a protected atmosphere for the swab 1. Optionally, in the inside, the container contains an inert gas, for example nitrogen. In an embodiment, the container is configured and specifically designed to be opened by means of a tear, such that it permits the opening towards the external environment. For example, the plastic material can be configured for providing a barrier to oxygen, capable of preventing the oxidation of the fragrance.

In an embodiment, the stopper 5 is realized starting from pellets or granule of polymeric material added with or including the fragrance. This not only ensures that the fragrance is distributed over all of the volume of the stopper 5 but also that this fragrance is uniformly distributed on all of the volume of the stopper 5.

The swab 1 is configured for be introduced at least partially within a container 7 for biological material that in a non-limiting embodiment comprises a body substantially test tube-shaped essentially cylindrical.

In a variant, the container 7 could comprise a conservation ground or other substance suitable for the purposes of the device.

The container 7 has, in correspondence of an its upper portion, a collar 11 to be able to house a closing element.

In particular, the closing element for the container 7 is the stopper 5 of the swab 1.

In FIG. 2 it is shown a first non-limiting embodiment of the container 7, wherein the collar 11 detects a transversal section of an area lower with respect to the area of the transversal section detected by the main portion of the body of the container. In detail, in this embodiment the collar 11 has a substantially cylindrical transversal section and is realized in a sufficiently elastic material to permit the removable coupling with the stopper 5 by means of a contrast insertion determining a sliding friction. This sliding friction is determined in an engagement surface, in particular a lateral engagement surface of the stopper 5.

It is observed, in detail, that the transversal section detected by the main portion of the body of container 7 is equal to the transversal section detected by the stopper 5. This permits to have a tactile and visual uniformity of the assembly container 7—stopper 5 when coupled.

In the embodiment of FIGS. 1 and 2, the engagement portion of the stopper 5 is configured for introducing in the collar 11. In the embodiment of FIGS. 1 and 2 the engagement portion of the stopper 5 comprises an annular recess configured for housing at least part of the collar 11. This annular recess is defined between a central portion of the engagement portion and a perimeter wall of the engagement portion.

The container 7 has a body provided with a lateral wall which extends itself axially along a predetermined direction and detects at least a portion having a transversal section of area substantially constant gradually moving axially along said predetermined direction.

The Applicant remarks that optionally the container 7 can have a shrinkage of the body destined to locally reduce the transversal section accessible to the swab 1, in particular to the collection element 3 and to the elongated body 2. Thanks to this aspect, it is possible to obtain a centering of the collection element 3 and the elongated body 2 within the container 7.

The embodiment shown in FIG. 5 has a collar 11 provided with a thread. The thread is specifically positioned in correspondence of an outer wall of the collar 11.

Also in this embodiment the transversal section has an area smaller with respect to the area of the transversal section detected by the main portion of the body of the container and this, when the transversal section detected by the main portion of the body of container 7 is equal to the transversal section detected by the stopper 5, allows to have a tactile and visual uniformity of the assembly container 7—stopper 5 when coupled.

In a preferred but non-limiting embodiment, the container 7 is realized in a plastic material, in particular in a material configured for not allowing the diffusion of said fragrance and/or configured not to absorb said fragrance. Preferably, but not limited thereto, said container 7 is transparent or translucent.

Since in use the plastic material of the body of the container can come into contact with the collection element 3, and can therefore also come into contact with saliva either directly or indirectly via the gel that can optionally be present, the technical characteristic of not permitting the diffusion of the fragrance or not absorbing said fragrance allows to optimally insulate the collection element 3 and the sample in use there collected from the fragrance itself.

The Applicant observes that this property is particularly useful where the stopper 5 is to be or remain mounted on the container 7 for a long time, as the diffusion of the fragrance into the container material can occur more easily in the long period.

Figure 6:
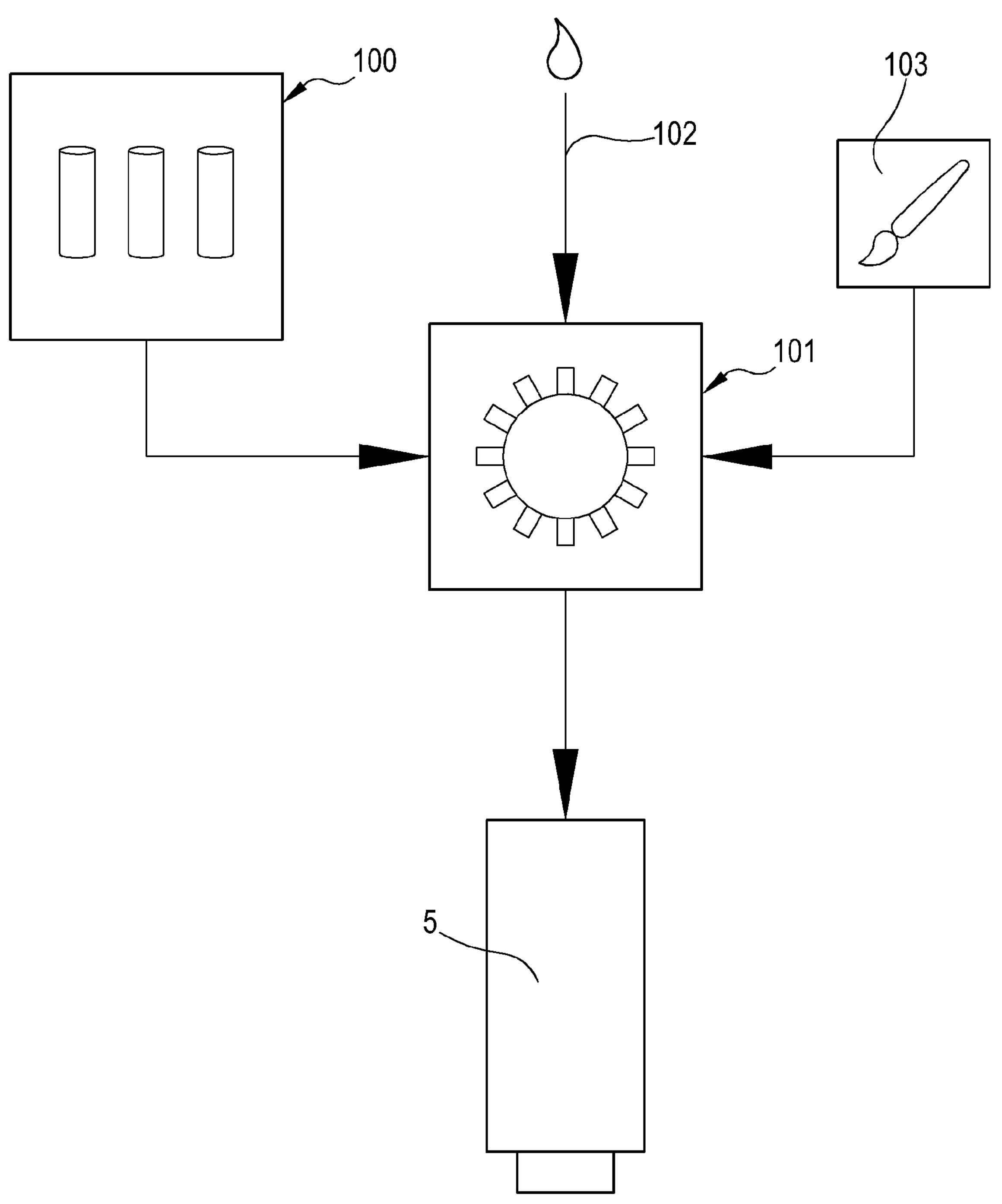
FIG. 6 shows a schematic view of the process of production of a stopper forming part of the swab for collecting samples of biological material.

As shown in FIG. 6, a method of production of the swab 1 comprises realizing the stopper 5 starting from pellets or granule 100 of polymeric material. The reference 101 indicates a machine destined to, in particular injection molding or compression molding or injection compression molding or co-molding of the stopper 5. The addition of the fragrance to the stopper 5 is such that, in use, the approaching of the stopper 5 to the nose, in particular the face, of the subject determines an increase in the production of the saliva. For the purposes of the present disclosure, "subject" is to be intended as a human being or an animal. The Applicant, indeed observes that the swab 1 can also be used for veterinary applications.

The reference 102 indicates the fragrance added to the mixture. In detail the addition of the fragrance 102 comprises the addition of pellets and/or granule and/or a fluid of fragrance, in particular of pellets and/or granule and/or a fluid containing a fragrance essential oil. In an embodiment, the fragrance pellets have a substantially cylindrical shape. The pellets, for example, can have a density substantially comprised between 0.2 $g/cm^3$ and 1 $g/cm^3$ or between 0.5 $g/cm^3$ and 0.7 $g/cm^3$.

In order in order to permit a correct maintenance of the fragrance, the fragrance is preferably essentially insoluble in water.

Although this should not be intended in a limiting manner, the fragrance is a fragrance compatible with food applications. This ensures a determined safety of use of the swab 1 even if inadvertently the stopper 5 comes into contact with the mouth.

The method of production of the swab 1 comprises in particular the mixing of the pellet or granule 100 of polymeric material with the fragrance. In particular, this mixing is destined to cause the production of a uniform mixture, wherein the fragrance is uniformly distributed in the pellet or granule 100, in particular being uniformly distributed therein in terms of volume.

In a preferred but non-limiting embodiment, the method therein described can further comprise the addition of a dye 103, thereby comprising mixing the dye 103 with the pellets or granule 100. The dye 103 can be added to the pellet or granule 100 of polymeric material and to the fragrance, substantially simultaneously or—alternatively —at a later time. Also with regard to the dye 103, the mixing is destined to cause the production of a uniform mixture, wherein the dye 103 is uniformly distributed in the pellet or granule 100 of polymeric material, in particular being uniformly distributed therein in terms of volume. Clearly, the dye 103 can be absent when the pellets or granule 100 of polymeric material already has the color of interest.

The Applicant has conceived various embodiments of the method described therein wherein various percentages in volume and/or weight of dye and/or fragrance can be added. Among these, some preferred embodiments comprise the addition of a percentage substantially comprised between 0.1% and 10% in weight or volume of fragrance 102, or between 0.5% and 7% in weight or volume of fragrance, in particular in a percentage substantially comprised between 1% and 6% in weight or volume of fragrance, more preferably between 2% and 5% in weight or volume of fragrance. Also, some embodiments provide for the addition of a percentage substantially comprised between 0.2% and 5% in weight or volume of dye, in particular between 0.5% and 4% in weight or volume of dye, more in particular between 1% and 3% in weight or volume of dye. Among the embodiments previously described, a particular and non-limiting embodiment provides for the mixing of 2% in weight or volume of dye with 4% in weight or volume of fragrance, and consequently provides for 94% in weight or volume of pellets or granule of polymeric material.

The Applicant underlines that various materials can be used for realizing the stopper 5. A non-exhaustive list of polymeric materials usable for realizing the stopper 5 comprises: polypropylene, polyethylene, PVC, polyester, polyamide, nylon, polystyrene.

Preferably, but not limited thereto, this polyethylene is a high-density polyethylene and/or is a polyethylene with antioxidant properties and/or is a polyethylene with high thermal stability during the step of transformation. This means that the volume variation of the high-density polyethylene described therein as a function of the temperature is particularly reduced, and this permits to obtain a considerable dimensional accuracy in the stopper 5, particularly when cooled. Furthermore, the preferably selectable polyethylene for realizing the stopper 5 has a melting temperature substantially comprised between 130° C. and 140° C., more preferably substantially equal to 135° C. The Applicant observes that the swab 1 therein described can be preserved for a long time in a refrigerated environment. For this reason, in an embodiment, the swab 1 therein described uses high-density polyethylene the embrittlement temperature thereof—in particular measured according to ASTM D 746 standard—is lower than −30° C., in particular lower than −40° C., more preferably lower than −50° C. This permits to preserve the swab 1 in the refrigerator or freezer without risk of weakening or breaking the stopper 5.

A specific and clearly non-limiting embodiment of polyethylene is Eraclene® ML 70 U by ENI.

In a non-limiting embodiment, this dye 103 is provided—in turn—in pellets of plastic material, preferably but not limited thereto of the same material with which the pellets and/or granule 100 of polymeric material are realized.

Although this should not be intended in a limiting manner, preferably the dye is a dye based on inorganic pigments, or on organic pigments, or on a combination of organic and inorganic pigments.

In particular, in an embodiment, the dye is provided in colored pellets of polyethylene, in particular of high density. In a preferred but non-limiting embodiment, this high-density polyethylene comprises Rifratene HDPE, produced by Rifra® Masterbatches. In particular this can be green Rifratene KE/2791.

Depending on the type of polymeric material used, the machine 101 can be adjusted to operate a molding at a predetermined temperature. In particular, it is observed that preferably, but in a non-limiting extent, the step of molding provides for a selection of a temperature substantially comprised between 150° C. and 300° C., more preferably substantially comprised between 160° C. and 280° C. It has been observed that the lower limit of the above-mentioned temperature ranges is given by the need to provide an adequate and sufficient heat to allow the melting of the pellets or granule of polymeric material, while the upper limit of the above-mentioned temperature ranges is given by the need to maintain almost unchanged, or not degrade—at least appreciably—the addition of the fragrance. In particular, it has been observed that operating a molding at temperatures lower than those of the above-mentioned lower limit risks to determine a worsening of the quality of the complete and uniform melting of the pellets or of the granule of plastic material; vice versa, operating a molding at temperatures higher than those of the above-mentioned upper limit risks to compromise the efficacy of the fragrance. The use of a minimum temperature of 150° C. with a polyethylene having a melting point substantially equal to 135° C. or in any case in the range 130° C.-150° C. ensures a sufficient temperature margin for a fair guarantee of complete melting.

Figure 7:
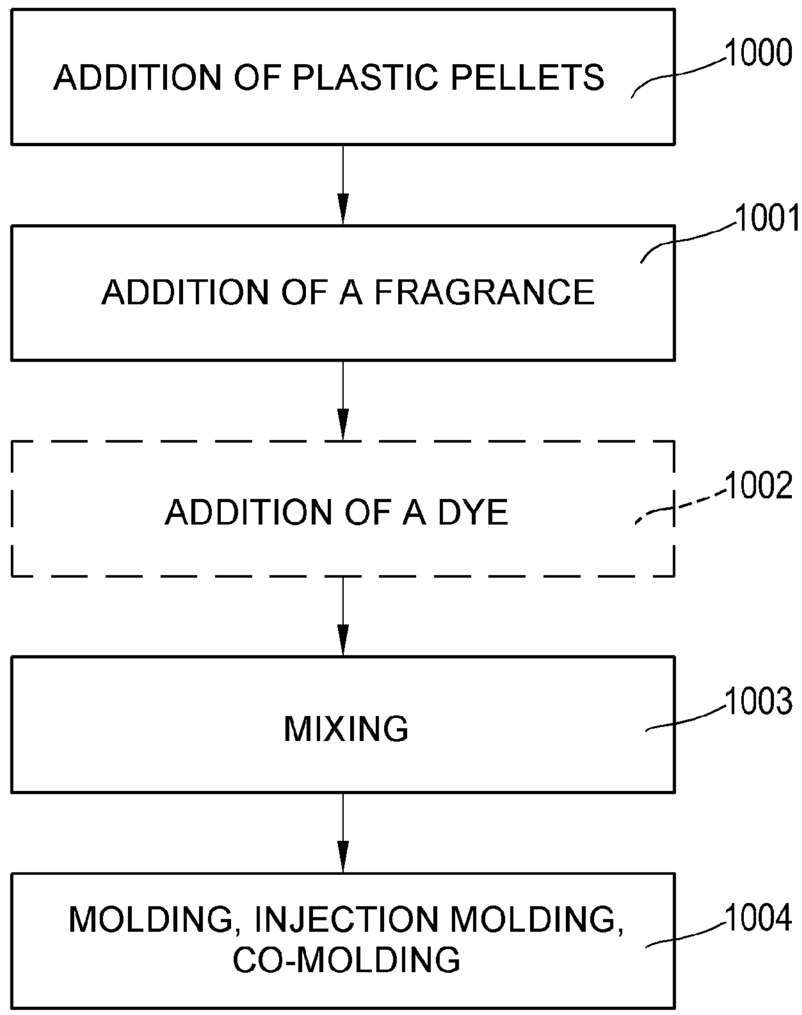
FIG. 7 shows a specific and non-limiting embodiment of a process of production of a stopper forming part of the swab of the present disclosure.

FIG. 7 shows a specific embodiment of a method of production of the swab 1 and it is described hereinafter.

The block 1000 of FIG. 7 identifies the step of addition of the pellets or granule 100 of polymeric material to the mixture that is used for realizing the stopper 5.

The block 1001 of FIG. 7 identifies a step of addition of the fragrance 102 to the mixture that is used for realizing the stopper 5.

The block 1002 of FIG. 7 identifies the step of addition of the dye 103 to the mixture that is used for realizing the stopper 5. It is important to note that the block 1002 is shown with a dotted line because the addition of dye 103 is not essential for the method described in this disclosure.

The block 1003 of FIG. 7 identifies the step of mixing the pellets or granule 100 of polymeric material, the fragrance 102 and—if present—the dye 103 in order to realize a mixture wherein these components are uniformly distributed.

The block 1004 of FIG. 7 identifies the step of molding carried out through the machine 101.

In particular, the method of molding permits to realize the stopper 5 with a hole so that, within this hole, the elongated body 2 can be at least partially introduced. Furthermore, the molding allows to realize the engagement surface or the thread previously described for the stopper 5. Alternatively, the method of molding allows to realize the stopper 5 and the elongated body 2 in a single piece.

The Applicant observes that according to the specific method of production following the step of molding there can be a step of assembly of the elongated body 2 with the stopper 5. This step of assembly can provide, in a non-limiting manner, a step of axial introduction of a portion of the elongated body within the previously realized hole.

Further steps not described in detail in the block diagram of FIG. 7 comprise the cooling of the intermediate or finished product realized by molding.

The disclosure is not limited to the embodiments shown in the attached figures. For this reason, reference signs that appear after elements or steps mentioned in the claims are provided for the sole purpose of increasing the intelligibility of the claims, and are not to be intended as limiting.

Additions, modifications or variants that are obvious to a person skilled in the art can be applied to the object of the disclosure, without falling outside the scope provided by the attached claims.

The invention claimed is:

1. A swab configured for collecting samples of biological material, comprising:

- an elongated body, having at least a portion with substantially axial development,
- a collection element configured for collecting samples of the biological material, positioned on the elongated body, wherein the collection element is configured for, and destined to, being introduced within a mouth of a subject and wherein the collection element comprises an absorbing material and is configured for collecting and retaining and/or preserving the sample of biological material, optionally a saliva of the subject,
- an engagement element, positioned in correspondence of a predefined portion of the elongated body, the engagement element being configured for being held, in use, by the subject and for being removably engaged with a container for the sample of biological material,
- wherein the engagement element comprises a fragrance and is configured for causing, in use, a stimulation of a production of the saliva when brought near a nose of the subject.

2. The swab according to claim 1, wherein said fragrance is distributed in at least part of a volume of the engagement element, in particular wherein said fragrance is uniformly distributed in said at least part of the volume of the engagement element.

3. The swab according to claim 1, wherein the engagement element is realized by mixing and subsequent melting at least pellets and/or granule of polymeric material and at least said fragrance, and/or wherein said fragrance is exclusively comprised in said engagement element.

4. The swab according to claim 1, wherein the engagement element comprises from 0.1% to 10% in weight or in volume of the fragrance or from 0.5% to 7% in weight or in volume of the fragrance, or from 1% to 6% in weight or in volume of the fragrance, or from 2% to 5% in weight or in volume of the fragrance.

5. The swab according to claim 1, wherein at least the engagement element comprises a dye, distributed in at least part of a volume of the engagement element, the dye being uniformly distributed in said at least part of the volume of the engagement element and/or wherein the engagement element comprises from 0.2% to 5% in weight or in volume of dye, or from 0.5% to 4% in weight or in volume of dye, or from 1% to 3% in weight or in volume of dye.

6. The swab according to claim 1, wherein the engagement element is realized by injection molding, compression molding or injection compression molding, or by co-molding, of pellets and/or granule of polymeric material and of at least a fragrance.

7. The swab according to claim 1, wherein the collection element is configured and sized for retaining in use an amount of fluid, wherein the absorbing material is configured for retaining in use an amount of the biological material, optionally saliva, comprised between 50 μl and 10 ml, or between 100 μl and 5 ml, or between 200 μl and 2 ml or between 500 μl and 1 ml, optionally wherein the collection element is a sponge element, and/or free from preserving substances.

8. The swab according to claim 1, wherein the engagement element is configured for being removably engaged with the container for the sample of biological material by contrast insertion and/or by screwing on said container for the sample of biological material.

9. A kit comprising a swab according to claim 1, and the container for the sample of biological material, said container comprising a cavity configured for containing at least a portion of said swab.

10. A method of production of a swab for collecting samples of biological material, comprising:

a step of production of an elongated body of the swab, said elongated body having at least a portion with axial development and being configured for supporting at least a collection element of the samples of biological material, optionally said biological material being a saliva of a subject, a step of production of the collection element, comprising realizing the collection element on the elongated body and/or followed by an assembly of the collection element on the elongated body, a step of production of an engagement element, configured for being held, in use, by the subject and configured for, and destined to, being removably engaged with a container for the sample of biological material, comprising realizing the engagement element on the elongated body and/or followed by an assembly of the engagement element to the elongated body, the step of production of the engagement element comprising an addition of a fragrance, such that, in use, an approaching of the engagement element to a nose of the subject determines a stimulation of a production of the saliva.

11. The method according to claim 10, wherein the step of production of the engagement element comprises a distribution of the fragrance in at least part of a volume of the engagement element.

12. The method according to claim 10, wherein the step of production of the engagement element comprises a mixing and a subsequent melting of at least pellets and/or granule of polymeric material and of at least said fragrance;

wherein the addition of the fragrance takes place exclusively in said engagement element.

13. The method according to claim 10, wherein the step of production of the engagement element comprises the addition of 0.1% to 10% in weight or in volume of fragrance or of 0.5% to 7% in weight or in volume of fragrance, or of 1% to 6% in weight or in volume of fragrance, or of 2% to 5% in weight or in volume of fragrance.

14. The method according to claim 10, wherein the step of production of the engagement element comprises the addition of a dye, and comprises the distribution of the dye in at least part of a volume of the engagement element.

15. The method according to claim 12, wherein at least the step of production of the engagement element comprises an injection molding or a compression molding or an injection compression molding, or by co-molding, of said pellets and/or granule of polymeric material and of at least said fragrance.

16. The method according to claim 12, wherein the addition of the fragrance comprises the addition of pellets and/or granule and/or a fluid of fragrance, optionally of pellets and/or granule and/or a fluid containing essential oil of the fragrance, wherein said molding, optionally the injection molding or compression molding or injection compression molding, or co-molding comprises a melting of said pellets and/or granule and of said fragrance that takes place at a temperature substantially comprised between 150° C. and 300° C., or between 160° C. and 280° C., or between 220° C. and 275° C. or between 240° C. and 260° C.

* * * * *